United States Patent
Rehse et al.

(10) Patent No.: US 11,344,249 B2
(45) Date of Patent: May 31, 2022

(54) DEVICE FOR NEUROVASCULAR STIMULATION

(71) Applicant: OTTO-VON-GUERICKE-UNIVERSITÄT MAGDEBURG, Magdeburg (DE)

(72) Inventors: Chris Rehse, Magdeburg (DE); Emrah Düzel, Magdeburg (DE); David Berron, Magdeburg (DE); Julian Haupenthal, Freiburg (DE)

(73) Assignee: NEOTIV GMBH, Magdeburg (DE)

( * ) Notice: Subject to any disclaimer, the term of this patent is extended or adjusted under 35 U.S.C. 154(b) by 1022 days.

(21) Appl. No.: 16/060,995

(22) PCT Filed: Dec. 13, 2016

(86) PCT No.: PCT/DE2016/100580
§ 371 (c)(1),
(2) Date: Jun. 18, 2018

(87) PCT Pub. No.: WO2017/101907
PCT Pub. Date: Jun. 22, 2017

(65) Prior Publication Data
US 2018/0360340 A1    Dec. 20, 2018

(30) Foreign Application Priority Data
Dec. 14, 2015    (DE) .................... 10 2015 121 763.5

(51) Int. Cl.
*A61B 5/377*    (2021.01)
*G06F 5/16*    (2006.01)
(Continued)

(52) U.S. Cl.
CPC ............ *A61B 5/377* (2021.01); *A61B 5/0205* (2013.01); *A61B 5/02438* (2013.01);
(Continued)

(58) Field of Classification Search
CPC ...................................................... A61B 5/377
(Continued)

(56) References Cited

U.S. PATENT DOCUMENTS

2015/0018630 A1    1/2015    Fotuhi
2015/0066104 A1    3/2015    Wingeier et al.

FOREIGN PATENT DOCUMENTS

WO    2015/027079 A1    2/2015

OTHER PUBLICATIONS

K. Schaaff, "Enhancing Mobile Working Memory Training By Using Affective Feedback", International Conference Mobile Learning, Mar. 1, 2013, pp. 269-273, Lisbon, Portugal.
(Continued)

*Primary Examiner* — Kesha Frisby
(74) *Attorney, Agent, or Firm* — WCF IP (57) ABSTRACT

The invention relates to a device for neurovascular stimulation, at least comprising: at least one brain activity sensor, at least one cardiovascular sensor, at least one computing unit and at least one output unit. The computing unit comprises at least one task algorithm, wherein signals of at least the brain activity sensor and the cardiovascular sensor can be received by the computing unit, and wherein a task, which is in correlation with at least the signals from at least the brain activity sensor and the signals of the cardiovascular sensor, can be determined by means of the task algorithm and can be output by means of the output unit.

9 Claims, 2 Drawing Sheets

(51) Int. Cl.
  *A61B 5/0205*  (2006.01)
  *A61B 5/00*  (2006.01)
  *G09B 7/02*  (2006.01)
  *A63B 22/02*  (2006.01)
  *G09B 19/00*  (2006.01)
  *A61N 1/36*  (2006.01)
  *A61B 5/024*  (2006.01)
  *G09B 23/28*  (2006.01)
  *A61M 21/00*  (2006.01)
  *G16H 20/30*  (2018.01)
  *A61B 5/374*  (2021.01)
  *A61B 5/16*  (2006.01)
  *A63B 24/00*  (2006.01)
  *A61B 3/113*  (2006.01)
  *A63B 71/06*  (2006.01)
  *A61B 5/021*  (2006.01)
  *A63B 22/00*  (2006.01)
  *A63B 22/06*  (2006.01)
  *A61N 1/04*  (2006.01)
  *A61B 5/375*  (2021.01)

(52) U.S. Cl.
  CPC .............. *A61B 5/163* (2017.08); *A61B 5/374* (2021.01); *A61B 5/4836* (2013.01); *A61M 21/00* (2013.01); *A61N 1/36* (2013.01); *A61N 1/36003* (2013.01); *A63B 22/02* (2013.01); *A63B 24/0062* (2013.01); *G06F 5/16* (2013.01); *G09B 7/02* (2013.01); *G09B 19/00* (2013.01); *G09B 23/28* (2013.01); *G16H 20/30* (2018.01); *A61B 3/113* (2013.01); *A61B 5/0022* (2013.01); *A61B 5/021* (2013.01); *A61B 5/375* (2021.01); *A61B 5/4839* (2013.01); *A61B 5/6803* (2013.01); *A61B 5/6817* (2013.01); *A61B 5/6898* (2013.01); *A61B 5/7405* (2013.01); *A61B 5/7445* (2013.01); *A61B 5/7455* (2013.01); *A61M 2021/005* (2013.01); *A61M 2021/0016* (2013.01); *A61M 2021/0022* (2013.01); *A61M 2021/0027* (2013.01); *A61M 2021/0072* (2013.01); *A61M 2205/3306* (2013.01); *A61M 2205/3375* (2013.01); *A61M 2205/3553* (2013.01); *A61M 2205/3569* (2013.01); *A61M 2205/3584* (2013.01); *A61M 2205/3592* (2013.01); *A61M 2205/505* (2013.01); *A61M 2205/507* (2013.01); *A61M 2209/088* (2013.01); *A61M 2230/04* (2013.01); *A61M 2230/06* (2013.01); *A61M 2230/10* (2013.01); *A61M 2230/18* (2013.01); *A61M 2230/205* (2013.01); *A61M 2230/30* (2013.01); *A61M 2230/432* (2013.01); *A61M 2230/65* (2013.01); *A61N 1/0452* (2013.01); *A63B 22/0048* (2013.01); *A63B 22/0076* (2013.01); *A63B 22/0605* (2013.01); *A63B 71/0619* (2013.01); *A63B 2024/0093* (2013.01); *A63B 2071/0625* (2013.01); *A63B 2220/806* (2013.01); *A63B 2220/807* (2013.01); *A63B 2220/808* (2013.01); *A63B 2220/836* (2013.01); *A63B 2225/50* (2013.01); *A63B 2230/045* (2013.01); *A63B 2230/06* (2013.01); *A63B 2230/10* (2013.01); *A63B 2230/105* (2013.01); *A63B 2230/30* (2013.01); *A63B 2230/65* (2013.01)

(58) Field of Classification Search
  USPC .......................................................... 434/322
  See application file for complete search history.

(56) References Cited

OTHER PUBLICATIONS

Takahashi et al., "Experimental Study toward Mutual Adaptive Interface", IEEE International Workshop on Robot and Human Communication, Jul. 18, 1994, Jul. 18, 1994, pp. 271-276.

Theill et al., "Effects of simultaneously performed cognitive and physical training in older adults", BMC Neuroscience, Mar. 5, 2015, pp. 1-14, vol. 14, No. 1.

DEVICE FOR NEUROVASCULAR STIMULATION

The invention relates to a device for neurovascular stimulation.

Methods for memory training are known from the prior art. US 2001/0066005 A1 for example describes a computer-implementable method for self-controlled learning. Neurophysiological states of the user are measured for the method, in order to give the user feedback on his self regulation or to adapt the learning environment.

The systems known from the prior art have the disadvantage that they are designed essentially for imparting knowledge and consequently it is only by chance, if at all, that they bring about a neuroplasticity, that is to say specifically directed stimulation for the new formation and interlinkage of nerve cells in the brain and/or for improving the vascular supply to the brain. Use of the known systems for the prevention or treatment of dementia is not possible with known systems.

The object of the invention is therefore to provide an improved device and a method for operating the device that preferably overcomes the stated disadvantages of the prior art.

The object is achieved according to the invention by means of a device for neurovascular stimulation as claimed in claim 1 and a method for controlling a device for neurovascular stimulation as claimed in claim 5. Further advantageous embodiments can be taken from the following description, the figures and the subclaims. However, the individual features of the embodiments described are not restricted to these, but can be combined with one another and with other features to form further embodiments.

A device for neurovascular stimulation is proposed, at least comprising at least one brain activity sensor, at least one cardiovascular sensor, at least one computing unit and at least one output unit. The computing unit comprises at least one task algorithm, wherein signals at least of the brain activity sensor and of the cardiovascular sensor can be received by means of the computing unit and a task which is in correlation with at least the signals at least of the brain activity sensor and the signals of the cardiovascular sensor can be determined by means of the task algorithm and can be output by means of the output unit.

For the purposes of the invention, the term neurovascular stimulation comprises a systematic stimulation using cognitive and physiological principles that are known from animal experiments to promote formation and interlinkage of nerve cells, in particular from neural stem cells or precursor cells, to improve the interlinkage of existing matured nerve cells and to improve a supply of blood to certain regions of the brain by vascular plasticity processes. Preferably, the regional distribution of the vascular plasticity in the brain in connection with a neuronal activity is controlled, regulated and/or induced, in order to induce it in connection with a neuroplasticity plasticity.

For the purposes of the proposed invention, the term brain activity sensor should be understood as meaning a sensor or a measuring device for determining a brain activity. In one embodiment, the brain activity sensor is at least a sensor selected from the group comprising an electroencephalography electrode—referred to hereinafter as an EEG electrode, a pupillometry sensor and/or a skin conductance sensor.

Preferably, the brain activity sensor is an EEG electrode, which more preferably can be placed in an ear, more preferably in the outer auditory canal of the ear. It is also preferably provided that the brain activity sensor has an earplug, which at least comprises the EEG electrode. Also preferably, the brain activity sensor comprises at least an inner-ear EEG electrode, as disclosed for example by EP 2 388 680 A1. Within the scope of this disclosure, reference is made to EP 2 388 680 A1 in full. It is also preferably provided that the brain activity sensor comprises headphones and/or a headset. More preferably, it is provided that the brain activity sensor comprises means for holding or fastening at least one sensor and/or an electrode on a head of a user. Particularly preferably, it is provided that the device comprises a number of brain activity sensors, for example a number of EEG electrodes. Particularly preferably, it is provided that the device comprises at least one reference electrode for at least one EEG electrode.

In a further embodiment it is provided that the brain activity sensor comprises at least one sensor for the analysis of eye movements, pupillometry, a sensor for measuring a flow of blood through the brain, preferably the cortex and/or a measurement of the autonomic nervous system. For example, a brain activity sensor is embodied as a near infrared spectroscopy sensor.

Within the scope of the description of the invention, electroencephalography is abbreviated to EEG.

The term cardiovascular sensor should be understood as meaning a sensor by means of which the pulse, heartbeat and/or blood pressure can be measured. For example, a heart rate watch or a chest strap comprises the cardiovascular sensor. In a further embodiment it is provided that the cardiovascular sensor comprises a sensor for an electrocardiogram and/or a blood pressure sensor. In one embodiment it is provided that at least two cardiovascular sensors are provided, which can be arranged in particular on a neck or a temple and on a wrist or ankle. Further data, for example a blood pressure, can be determined from a difference or a relation of pulse data obtained by means of the sensors.

Enumerations given by way of example within the description of the invention should not be regarded as exhaustive.

The computing unit may for example be a computer, a cell phone, in particular a smartphone, a tablet computer and/or a microcomputer. In one embodiment it is provided that the computing unit comprises a server, which is preferably integrated in a network to which the device has access. More preferably, the device has a means of connection to the network in which the computing unit is integrated. In one embodiment, the means of connection is a mobile device with Internet capability, for example a cell phone.

Preferably, the computing unit is connected to a network, for example the Internet. In a further embodiment, the computing unit is connected directly to further components of the device. More preferably, it is provided that the computing unit comprises a smartwatch. In particular, the smartwatch comprises at least one sensor, at least one actuator—such as for example a vibration motor and in particular a computer functionality and/or connection to a computer.

The output unit comprises for example a monitor, a display, a display fastened to the head—such as for example video glasses or virtual reality glasses and/or a device for displaying augmented reality, such as for example augmented reality glasses. In a further embodiment it is provided that the output unit comprises an audio output, for example headphones and/or a loudspeaker.

It is also provided in one embodiment that the output unit comprises a sensory output, for example by means of a vibration motor. In a further embodiment it is provided that the output unit has a controller for a training device, for example a cardio device; preferably, parameters of the training device are controllable. In particular, a performance resistance and/or a further parameter of a training device is controllable by means of an output of the device.

In a further embodiment it is provided that the output unit has a controller for a device for electrical muscle stimulation. In a further embodiment it is provided that the output unit has a means for the output of odors and/or images taken of facial expressions.

For a long time the view was held that neuroplasticity, that is to say a stimulation for the new formation and/or interlinkage of nerve cells in the brain, is not possible. The devices for so-called brain training that are known from the prior art therefore aim exclusively at improving specific learning effects. The device according to the invention takes into account the realization that in the adult brain there are neural stem cells that allow a new formation of neurons and their interlinkage. Newly formed neurons that are not immediately interlinked die off again and have no long-term effects, for example for the treatment or prevention of dementia disorders. However, neuroplasticity preferably takes place under certain conditions, which can be advantageously determined and/or produced by means of the device. Particularly advantageously, a certain cardio exertion and a certain brain activity, which advantageously occur together, are helpful or necessary for neuroplasticity.

Also advantageously, the device determines at least on the basis of the measured signals by means of a task algorithm a task that is set for the user by means of the output unit. The task is selected in such a way that it is in correlation with the signals determined. In one embodiment it is provided that at least one relation of the signals of the brain activity sensor and the signals of the cardiovascular sensor dictates the task.

The task is selected by means of the task algorithm in particular in such a way that, by engaging in the task, the brain of the user is induced, in particular under the influence of the cardio exertion, to form new neurons and to interlink more preferably these new neurons more preferably in addition the already matured existing neurons in particular with one another.

The task is preferably adapted to the user. In a particularly preferred embodiment it is provided that the task is selected in such a way that the user can solve the task.

In a further embodiment it is provided that the task algorithm includes at least one answer to the task by the user in the determination of a further task, in particular the task algorithm takes into consideration whether the user has correctly or incorrectly answered a previous task. It is also preferably provided that the task algorithm takes into consideration a time that has elapsed between the output of the previous task and an input of the answer.

In one embodiment, the task is selected from various task complexes. A task complex is at least selected from a group comprising mnemonic tasks, a Stroop test, a reading task, melody recognition, a coordination task, pattern recognition, pattern separation, pattern completion, a memory task—in particular a task that addresses the procedural and/or declarative, preferably the episodic memory, a task that requires precise encoding, novelty detection, simple linking, forward linking—in particular transitive inference, generalization, a salient stimulus—in particular an emotionally salient stimulus, a task with its own stimuli and/or a request for a greater or lesser effort to be made—for example to run slower or faster, a navigation task, a multitasking task with requirements for executive control, a working memory task and/or task for the visual or auditory discrimination of similar stimuli.

In one embodiment, own stimuli are photos or videos of situations, places or persons that the user knows.

In a further embodiment it is provided that the user is exposed to at least one stimulus, such as for example an odor, an image, a color, a pattern, a sensory stimulus, a melody and/or a noise.

Particularly preferably, it is provided that the task is selected from at least one stimulus. In particular, it is provided that the task is at least one stimulus. In a further embodiment it is provided that one or more tasks from one or more task complexes can be combined. In a further embodiment it is provided that a number of stimuli can be combined. In a further embodiment it is provided that at least one stimulus can be combined with at least one task from at least one task complex. In a further embodiment, unexpected or deviant stimuli are passively presented. In a further embodiment, unexpected and/or deviant stimuli are presented and must be actively detected. In a further embodiment, stimulus/reward associations are learned in the sense of reinforcement learning and are flexibly relearned; this is known as reversal learning.

For example, one embodiment provides that the output of at least one task with its own stimuli comprises taking photos, in particular randomly taking of photos, before the use of the device. In one embodiment it is provided that a camera, in particular a camera carried by the user, takes photos, preferably automatically, over a time period before the use of the device that are shown during the use of the device. In particular, the setting of a task may comprise chronologically sorting the images. In a further embodiment it is provided that the images and further images that are not taken by the user's camera are shown.

Particularly advantageously, use of the device according to the invention in the prevention of dementia and/or the treatment of dementia is envisaged. In one embodiment it is provided that the task algorithm includes the type of dementia disorder of the user in a determination or generation of the task. In a further embodiment it is provided that the device can be used for increasing brain capacity. One embodiment provides that in particular the user can prescribe an objective for the brain capacity. An objective comprises for example an aim selected from a group comprising improving memory—in particular improving the declarative memory, improving pattern recognition, improving pattern separation, improving orientation, improving perception, improving speech, improving concentration and/or improving logic. The objective can preferably be entered into the device by means of an input device.

In one embodiment it is provided that the device comprises at least one input device. In particular, an input device comprises at least one means of input selected from a group comprising a joystick, a keypad, a touchpad, a brain signal feedback, a means for determining the eye movement—an eye tracker, a gyroscope, a brain signal, a microphone and/or a button or a buzzer.

In one embodiment it is provided that user data, the objective and/or an answer to the task set can be entered by means of the input device. User data comprise for example the age, sex, disorder, medication and/or further data of the user. Preferably, user data comprise pulse data and/or neuronal data, which can in particular be determined during the use of the device. In a further embodiment, user data comprise data determined, measured and or entered during the use of the device. In one embodiment it is provided that the user data are included in the task algorithm in order to determine the task.

A further embodiment provides that the device comprises a cardio device. A cardio device is preferably a device selected from a group at least comprising a treadmill, a cross trainer, a rowing machine, an ergometer, a stepper, an abdominal trainer, an omnidirectional treadmill and/or a spinning device. In a further embodiment, the device additionally or alternatively comprises an electrostimulation device. Advantageously, the device is embodied in such a way that it controls the cardio device and/or the electrostimulation device in such a way that the user in particular achieves, and preferably maintains over a period of time, a pulse rate that is optimum for neuroplasticity.

In one embodiment the device additionally has a spirometer, with which the setting of the optimum training level can be accurately adapted on the basis of the concentration of $CO_2$ in the respiratory air. More preferably, the device controls the cardio device and/or the electrostimulation device in such a way that, in particular by making an effort or relaxing, the user achieves in particular a brain activity that is essentially optimum for neuroplasticity.

More preferably, the device controls the cardio device and/or the electrostimulation device in such a way that a user achieves a heart rate or pulse rate and/or $CO_2$ concentration in the respiratory air that is optimum for the measured brain activity for neuroplasticity. In a further embodiment it is provided that the device controls the cardio device and/or the electrostimulation device while taking into consideration the user data.

For the purposes of the invention, control should also be understood as meaning feedback control.

Particularly preferably, neuronal data can be generated from the signals of the brain activity sensor by means of the computing unit. More preferably, pulse data can be generated from the signals of the cardiovascular sensor by means of the computing unit. A further embodiment provides that at least neuronal data from the signals of the brain activity sensor and pulse data from the signals of the cardiovascular sensor can be set in relation to one another by means of the task algorithm.

In a further embodiment it is provided that medicaments are given in an automated manner. In one embodiment, the device has a device for administering medicaments. In one embodiment it is provided that medicaments can be administered in dependence on the neuronal data and/or the pulse data, possibly while taking into consideration the user data.

A method according to the invention for controlling a device for neurovascular stimulation is also proposed. The device comprises at least one brain activity sensor, at least one cardiovascular sensor, at least one computing unit and at least one output unit. The computing unit comprises at least one task algorithm, wherein signals at least of the brain activity sensor and of the cardiovascular sensor are received by means of the computing unit and at least a task which is in correlation with at least the signals at least of the brain activity sensor and the signals of the cardiovascular sensor is determined by means of the task algorithm and is output by means of the output unit.

Preferably, the task algorithm determines the task. In a further preferred embodiment, the task algorithm determines a number of tasks. Preferably, the task algorithm keeps determining new tasks. Also preferably, the task algorithm determines a further task once the user has answered a task or a prescribed time since the output of the last task has elapsed. In a further embodiment it is provided that a new task is determined and preferably output when for example it is evident from the neuronal data that the user is no longer engaged in the task. The task is preferably always determined with reference to the current neuronal data and pulse data.

It is also preferably provided that the task algorithm sets various values, for example a number of sensorially determined values and/or a number of user data, in relation to one another in order to determine a task. Also preferably, the task algorithm comprises at least one table with tasks or task complexes from which the task algorithm selects a task. In a particularly preferred embodiment, the task algorithm is a piece of software. It is also preferably provided that the task algorithm determines a task from a number of tasks that are stored on the computing unit. Also preferably, the computing unit comprises at least one table that is accessed by the task algorithm. In one embodiment it is provided that the task algorithm comprises a function which outputs a task in dependence on values that are entered and/or measured. In one embodiment it is provided that at least one task is selected by means of the task algorithm from at least one task complex. Also preferably, the task algorithm matches the task to the user data.

In a further embodiment it is provided that neuronal data are determined from the signals of the brain activity sensor. Preferably, at least one frequency band of an EEG is determined, or its presence is verified. Also preferably, an amplitude of at least one frequency band is determined. In one embodiment it is provided that a deviation of an optimum brain activity for the neoplasticity of the user is determined. It is also preferably provided that a deviation from an EEG frequency band that is optimum for the neuroplasticity of the user is determined.

In one embodiment it is provided that a scanning rate of the signals at the brain activity sensor of approximately 1 Hz to approximately 600 Hz, preferably approximately 2 to approximately 300 Hz, is used. In one embodiment it is provided that EEG frequency bands from delta to gamma are determined. Preferably, at least the delta frequency band from approximately 0.5 Hz to approximately 4 Hz is determined. Also preferably, at least the theta-1 frequency band from approximately 4 Hz to approximately 6.5 Hz is determined. Also preferably, at least the theta-2 frequency band from approximately 6.5 Hz to approximately 8 Hz is determined. Also preferably, at least the alpha frequency band from approximately 8 Hz to approximately 13 Hz is determined.

Also preferably, at least the low beta frequency band from approximately 13 Hz to approximately 15 Hz is determined. Also preferably, at least the mid beta frequency band from approximately 15 Hz to approximately 21 Hz is determined. Also preferably, at least the high beta frequency band from approximately 21 Hz to approximately 30 Hz is determined. Also preferably, at least the gamma frequency band from approximately 30 Hz to approximately 80 Hz is determined.

In one embodiment it is provided that the user is set at least one learning task by means of the device in an encoding mode. The learning task may be for example a sequence of images that the user has to remember. It is particularly advantageously provided that the device only sets the learning task when the device determines an increase in the amplitude in a frequency band from approximately 3 Hz to approximately 8 Hz, preferably approximately 4 to approximately 8 Hz, more preferably the theta-1 frequency band and/or the theta-2 frequency band, preferably an increase in the amplitude by at least approximately 10%, more preferably at least approximately 20%, with respect to a previously determined reference amplitude, more preferably at an amplitude of above approximately 20 µV, more preferably above approximately 50 µV, more preferably above approximately 70 µV.

In a further embodiment, a user-specific reference amplitude and a user-specific exceeding of the reference amplitude are determined in advance as a threshold value for initiating the determination of the task or are determined and/or adapted by the use of the device. According to one embodiment, the reference amplitude is determined in a rest phase, for example during sleep or when the user has approximately his resting pulse rate, or in a further embodiment when working on a task. For the calculation of the reference amplitude, preferably an average amplitude value is over a time period of a few milliseconds, for example approximately 10 ms to approximately 90 ms, to several minutes, for example approximately 2 minutes to approximately 15 minutes. According to one embodiment, the reference amplitude may be used as a constant variable over a number of uses or, according to a further embodiment, be newly determined dynamically from use to use and/or repeatedly within one use.

In a further embodiment it is provided that, in a recall mode, a memory task is set. Preferably, the memory task comprises remembering at least parts of the learning task previously set. It is also preferably provided that the device only sets the memory task when the device determines an increase in the amplitude in a frequency band from approximately 3 Hz to approximately 8 Hz, preferably approximately 4 to approximately 8 Hz, more preferably the theta-1 frequency band and/or the theta-2 frequency band, preferably an increase in the amplitude by at least approximately 10%, more preferably at least approximately 20%, with respect to a previously determined reference amplitude, more preferably at an amplitude of above approximately 20 µV, more preferably above approximately 50 µV, more preferably above approximately 70 µV. In a further embodiment, a user-specific reference amplitude and a user-specific exceeding of the reference amplitude are determined in advance as a threshold value for initiating the determination of the task or are determined and/or adapted by the use of the device.

In a further embodiment it is provided that, in particular while a task is being output, at least the alpha frequency band and/or the beta frequency band is determined. It is also preferably provided that the task is adapted when there is a change in the alpha frequency band and/or the beta frequency band. If, for example, it is determined on the basis of a change in a frequency band, preferably the alpha frequency band and/or the beta frequency band, that there is a frustration, in particular a subliminal frustration—that is to say a frustration reaction below the perception threshold of the user, excessive demand and/or a punishment reaction, the task is adapted. For example, a sequence of images to be recalled is slowed down and/or the frequency of the sequence is not speeded up.

Furthermore, in one embodiment the task is set and/or adapted in such a way that a reward reaction, in particular a release of endorphins, is initiated. Furthermore, in one embodiment the task is set and/or adapted in such a way that a brain signal typical of a reward expectation and/or reward prediction error is measured. Advantageously, the task is regulated on the basis of the brain signal. In particular, the task is in particular adapted by the neuronal data in such a way that the user can solve it.

In a further embodiment it is provided that a reward reaction and/or frustration, in particular subliminal frustration, excessive demand and/or a punishment reaction is determined by means of near infrared spectroscopy. For example, near infrared spectroscopy is carried out at least in a region of at least one temporal lobe.

In a further embodiment it is provided that a monitoring and/or storage of the signals from the brain activity sensor or of the neuronal data takes place. It is also provided in one embodiment that a storage of the signals of the cardiovascular sensor or of the pulse data takes place. It is preferably provided that user data are determined on the basis of the neuronal data and/or the pulse data.

For example, an adaptation of the task on the basis of user data that contain pulse data and/or neuronal data at least of one previous measurement or use of the device is envisaged. In a further embodiment it is provided that an adaptation of the task takes place in situ, that is to say during the use of the device. In a further embodiment it is provided that the device supports and/or automatically carries out diagnostics, in particular of dementia disorders. In a further embodiment it is provided that diagnostics, medication and/or a recommendation of medication takes place on the basis of the user data determined.

In a further embodiment it is provided that an amplitude of an evoked potential is determined. Preferably, an evoked potential is determined on the basis of a visual, auditory, olfactory, gustatory and/or tactile information presentation, preferably approximately 10 ms to approximately 3000 ms, more preferably approximately 100 ms to approximately 1000 ms, after the beginning of the information presentation. It is also preferably provided that a discrimination of new and known information takes place by means of the evoked potential determined. For example, it can be determined by means of the evoked potential whether the user recalls an item of information, preferably independently of whether the user perceives it consciously. Preferably, the task is adapted on the basis of at least the evoked potential determined, preferably taking into consideration the information presentation.

In a further embodiment it is provided that the amplitude of the alpha frequency band is determined in particular in a time window from approximately 100 ms to approximately 3000 ms, more preferably approximately 100 ms to approximately 1000 ms, after the beginning of the information presentation. It is also preferably provided that a discrimination of new and known information takes place by means of the amplitude of the alpha frequency band. Preferably, the task is adapted on the basis of at least the amplitude of the alpha frequency band, preferably taking into consideration the information presentation.

In a further embodiment it is provided that the amplitude of the theta-1 frequency band is determined in particular in a time window from approximately 100 ms to approximately 3000 ms, more preferably approximately 100 ms to approximately 1000 ms, after the beginning of the information presentation. It is also preferably provided that a discrimination of new and known information takes place by means of the amplitude of the theta-1 frequency band. Preferably, the task is adapted on the basis of at least the amplitude of the theta-1 frequency band, preferably taking into consideration the information presentation.

In a further embodiment it is provided that the amplitude of the theta-2 frequency band is determined in particular in a time window from approximately 100 ms to approximately 3000 ms, more preferably approximately 100 ms to approximately 1000 ms, after the beginning of the information presentation. It is also preferably provided that a discrimination of new and known information takes place by means of the amplitude of the theta-2 frequency band. Preferably, the task is adapted on the basis of at least the amplitude of the theta-2 frequency band, preferably taking into consideration the information presentation.

For the purposes of the invention, the term information should be understood as meaning at least one item of visual, auditory, olfactory, gustatory and/or tactile information.

Evoked potentials are differences in potential in the signals determined by the brain activity sensor that are initiated by a stimulation of a sensory organ or peripheral nerve. Preferably, all deliberately initiated electrical phenomena in the EEG are evoked potentials. Evoked potentials preferably have amplitudes of approximately 0.5 µV to approximately 20 µV, more preferably approximately 1 µV to approximately 15 µV.

In a further embodiment it is provided that a perfusion, that is to say throughflow of blood, of a region of the brain is determined for example by means of near infrared spectroscopy. It is also preferably provided that a discrimination of new and known information takes place by means of the determined perfusion of the region of the brain. Preferably, the task is adapted on the basis of at least the determined perfusion of the region of the brain, preferably taking into consideration the information presentation.

In a further embodiment it is provided that pulse data are determined from the signals of the cardiovascular sensor. Pulse data may be for example a heart rate, a retrograde pulse rate, an anterograde pulse rate, a peripheral pulse deficit and/or a blood pressure.

In a particularly preferred embodiment, a deviation from an individual training pulse is determined. For example, a maximum pulse of the user is preferably determined in advance of the use of the device. The maximum pulse may be determined in relation to the age of the user, for example by the formula maximum pulse=220−age in years.

In one embodiment, further user data may be included in the calculation of the maximum pulse. It is preferably provided that the maximum pulse is determined by means of a training unit that the user preferably completes in advance of the use of the device. The training pulse is in particular the pulse that is optimum for the neuroplasticity in the brain of the user. Preferably, the training pulse is in relation to the maximum pulse. For example, the training pulse is approximately 30% to approximately 70% of the maximum pulse, preferably approximately 40% to approximately 60%, more preferably approximately 40% to approximately 50%. In a further advantageous embodiment, the concentration of $CO_2$ in the respiratory air and/or the oxygen content in the blood is measured. Further advantageously, a training pulse is set in such a way that the user is at the anerobic threshold.

When the term "approximately" is used within the context of the invention, it should be understood as meaning a tolerance range that a person skilled in the art considers to be customary in this field; in particular, a tolerance range of ±20%, preferably ±10%, is envisaged. The term "essentially" also indicates a tolerance range that is acceptable for a person skilled in the art from commercial and technical aspects, and so the corresponding feature should also be recognized as such.

In one embodiment it is provided that, in the event of a deviation from the brain activity that is optimum for neuroplasticity, the user is stimulated in order to achieve essentially the brain activity that is optimum for neuroplasticity. A stimulation may take place for example by means of a task, which is output in particular by means of the output unit. In a further embodiment it is provided that the stimulation is at least an inducement or request to the user, in particular by means of the output unit, to produce a physically greater or lesser performance. For example, in one embodiment it is provided that a performance resistance of the cardio device is changed. In a further embodiment it is provided that a change in the brain activity is induced by means of brain-internal, brain-external and/or extracranial current pulses. In a further embodiment it is provided that a change in the brain activity is induced by means of brain-internal, brain-external and/or extracranial magnetic fields. In a further embodiment it is provided that in particular a number of measures are provided in order to achieve essentially the optimum brain activity of the user for neuroplasticity.

The brain activity is determined at least from one or more signals or items of data selected from a group comprising at least one electrical signal, preferably an EEG signal, in the form of evoked potentials and/or averaged oscillations of an EEG frequency band, a change in perfusion in at least one region of the brain, pupil diameter and/or viewing direction. In one embodiment it is provided that values for the optimum brain activity of the user for neuroplasticity are determined during or before the use of the device; in particular, the optimum values are those that are established during expectation of novelty, for example new images, new odors, new sounds and/or expectation of reward, for example points in a game. Preferably, the optimum brain activity is determined specifically for the user. In particular, an optimum brain activity is determined from the user data preferably determined during the use of the device. For example, one or more tasks is/are performed, possibly repeatedly, with different pulse data and neuronal data and the optimum brain activity is determined.

In a further embodiment it is provided that, in the event of a deviation of the pulse of the user from the prescribed training pulse, the user is stimulated in order to achieve approximately the training pulse. In a further embodiment it is provided that the stimulation is at least an inducement or request to the user, in particular by means of the output unit, to produce a physically greater or lesser performance. For example, in one embodiment it is provided that a performance resistance of the cardio device is changed. In a further embodiment it is provided that the user is brought essentially to a training pulse by means of an electrostimulation device.

In one embodiment it is provided that a task is determined at least on the basis of a relation of at least one pulse data element to at least one neuronal data element from the task algorithm. In a further embodiment it is provided that the task algorithm determines the task by means of at least one user data element. Preferably, the at least one user data element is set in relation to at least one pulse data element and at least one neuronal data element in order to determine the task. In a further embodiment it is provided that at least a number of relations of the pulse data to the neuronal data are respectively assigned to at least one task or a task complex. It is also advantageously provided that a task is only determined by the task algorithm when the relation of the pulse data and neuronal data are approximately constant over a defined time, for example approximately 10 s to approximately 90 s, preferably approximately 20 s to approximately 60 s, more preferably approximately 30 s to approximately 40 s.

In a further embodiment it is provided that a task is determined by means of the task algorithm at least in correlation with an input by means of an input device. If, for example, an incorrect input is entered as an answer to the task, the next task is made easier. It is also provided in one embodiment that the task is determined by means of the task algorithm at least in correlation with a time difference between an output of the task and the input of the answer. In a further embodiment it is provided that a task is determined in correlation with a specific eye movement.

It is also provided in one embodiment that the object is set when there is a specific eye movement. It is also provided in one embodiment that a task is set when specific neuronal data are determined.

The input may take place by means of a joystick, a keypad, a touchpad, a brain signal feedback, a means for determining the eye movement, a gyroscope, a brain signal, a microphone and/or a button. In one embodiment it is provided for example that at least one brain signal, for example at least one EEG signal, is used in order to instigate the input.

In a further embodiment it is provided that the task algorithm is adapted on the basis of the user data of one or more users.

In a further embodiment it is provided that a performance resistance of the cardio device is controlled at least on the basis of a relation of at least one pulse data element to a neuronal data element. It is also provided in one embodiment that the electrostimulation device is controlled at least on the basis of a relation of at least one pulse data element to a neuronal data element.

In a further embodiment it is provided that a situation is recorded in advance of the use of the device by means of at least one camera and/or at least one microphone and is output by means of the output unit. Preferably, an everyday situation from the everyday life of the user is output. In a further embodiment it is provided that a sporting situation or an environment, in particular from the viewpoint of the user or a third party, is recorded and is output as a task, as an alternative to a task or in connection with a task, during the use of the device. For example, it is provided that a user goes on a hike and takes along a camera, which takes photos and/or makes video recordings during the hike. During the use of the device, the images and/or films are played in order to stimulate recollections and/or to ask the user questions in relation to the photos shown and/or videos played, preferably automatically by the device, more preferably in dependence on at least one of the pulse data and the neuronal data. In a further embodiment it is provided that the photos and/or videos are synchronized with a movement on the cardio device. Thus, the user may for example advantageously run the route of the hike in virtual reality.

A camera is preferably a digital camera, for example a CCD camera. In a further embodiment it is provided that the camera comprises a 3D camera system, for example a stereo camera, a camera with a triangulation system, a camera with a photomixing detector, a camera with an interferometer and/or a light-field camera. It is also provided in one embodiment that the camera comprises a panoramic camera, for example a rotating camera, a line-scan camera, a camera with at least one wide-angle or fisheye lens and/or a camera with a mushroom mirror. In a preferred embodiment it is provided that the camera is a 360 cam from the company Giroptic Inc.

In a further embodiment it is provided that a number of devices are interlinked with one another. In a further embodiment it is provided that at least two users use the devices jointly. In particular, it is provided in one embodiment that the users solve a task or a number of tasks jointly and/or in opposition to one another, in particular play with one another. The users can, according to one embodiment, measure themselves, compete against one another and/or act cooperatively in solving the tasks. In particular, the cardiovascular activity has to be performed by each user, preferably in accordance with his user profile.

Further advantageous embodiments emerge from the following drawings. However, the developments shown there should not be interpreted as restrictive, but rather the features described there can be combined with one another and with the features described above to form further embodiments. Furthermore, it should be pointed out that the reference signs given in the description of the figures do not restrict the scope of protection of the present invention, but instead merely refer to the exemplary embodiments shown in the figures. The same parts or parts with the same function have the same reference signs hereafter. In the drawing:

Figure 1:
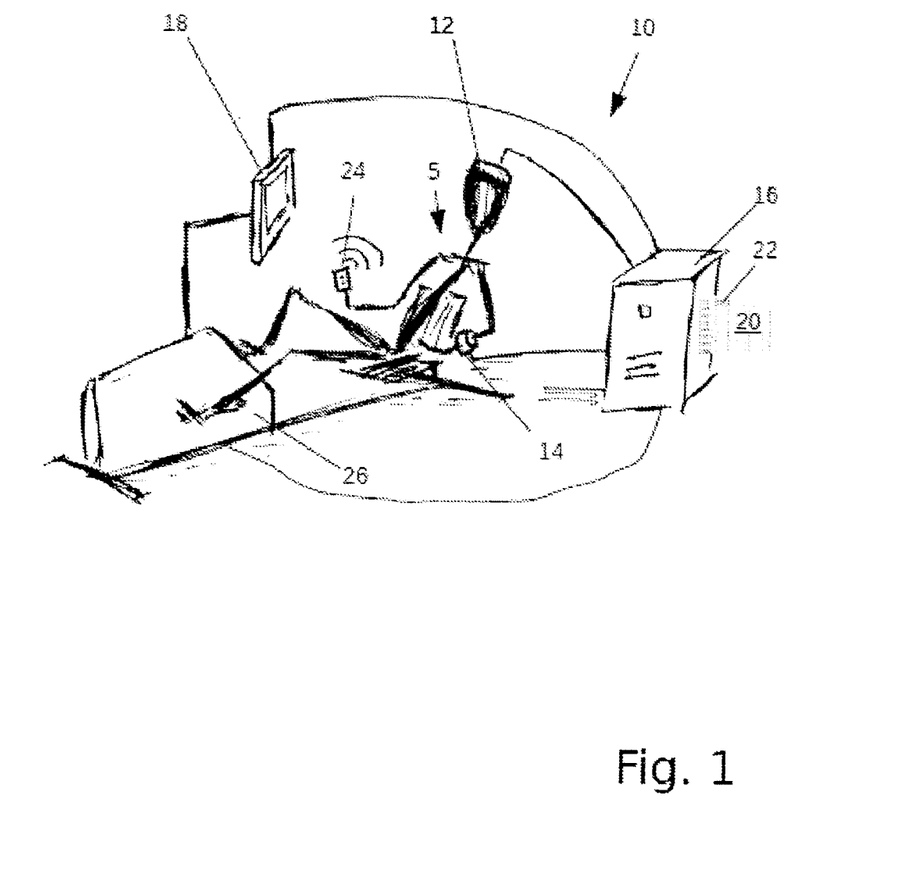
FIG. 1 schematically shows a first embodiment of a device according to the invention.

FIG. 1 schematically shows a device 10 for neurovascular stimulation. It comprises a number of brain activity sensors 10, which are designed for picking up EEG signals on the surface of a head. The device 10 also comprises a cardiovascular sensor 14, which for example measures a pulse on the lower arm and/or a blood pressure. Measured values of the brain activity sensors 10 and of the cardiovascular sensor 14 that are recorded are transmitted to a computing unit 16, which converts the measured values into neuronal data and pulse data. By means of a task algorithm 20, at least the pulse data and the neuronal data are set in relation to one another, preferably with further user data. The task algorithm 20 determines from this a task 22, which is stored in the computing unit 16 and is output by means of an output unit 18, which in FIG. 1 is designed as a monitor. A user 5 who is using the device 10 operates a cardio device 26, in order to achieve a training pulse. Preferably, the computing unit 16 controls the cardio device 26 in such a way that the user 5 essentially achieves and preferably essentially maintains the training pulse. For example, the computing unit 16 controls a performance resistance of the cardio device 26. If the computing unit 16 determines from the pulse data that the training pulse individual to the user has been essentially achieved, and determines from the neuronal data that there is essentially a brain activity that is conducive to neuroplasticity, the task 22 determined by means of the task algorithm 20 is output by way of the output unit 18. The user 5 then enters an answer to the task 22 by means of an input device 24. Preferably, the input device 24 transmits the answer of the user 5 to the computing unit 16. After that, in one embodiment the setting of at least one further task 22 takes place, preferably newly determined by means of the task algorithm 20 from the pulse data and the neuronal data.

Figure 2:
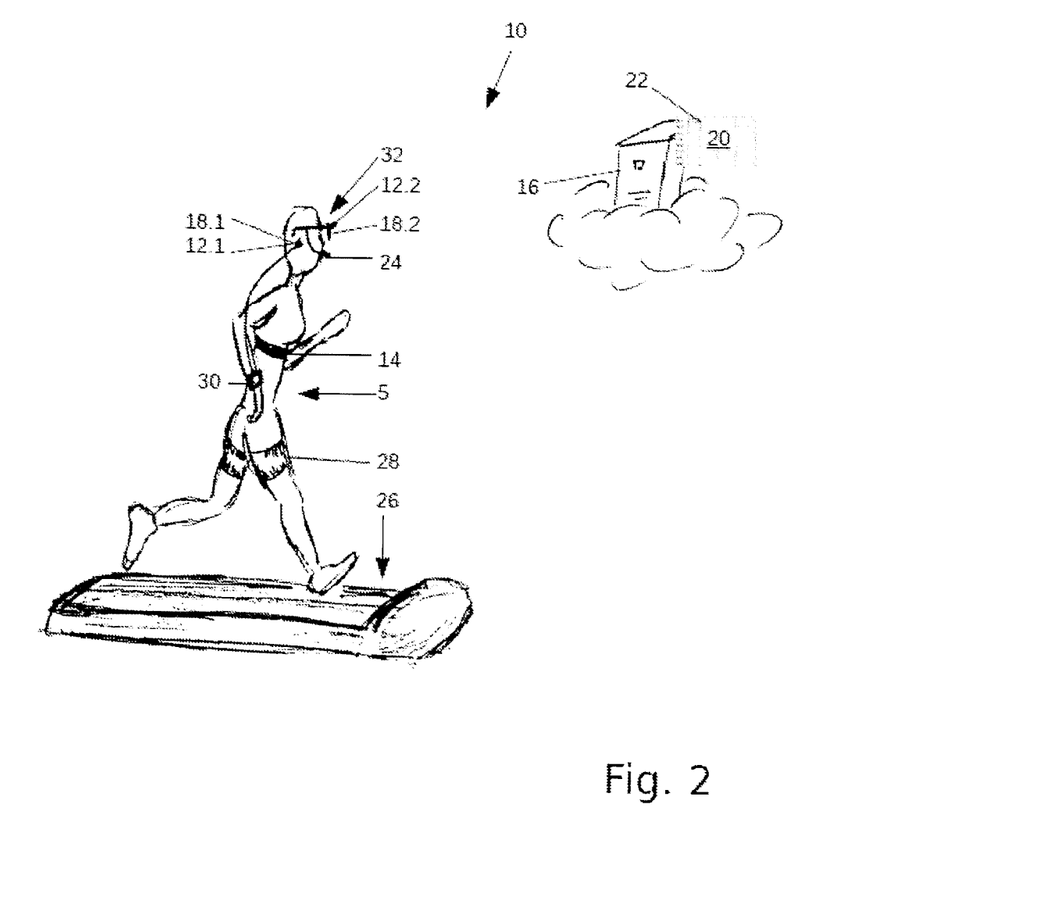
FIG. 2 schematically shows a further embodiment of a device according to the invention.

FIG. 2 schematically shows a further embodiment of the device 10. It comprises a brain activity sensor 12.1, which is designed as in-the-ear headphones. The in-the-ear headphones act at the same time as an acoustic output unit 18.1. The brain activity sensor 12.1 is connected to a computer that can be worn on the arm, a smartwatch 30. The smartwatch is also connected in a cable-bound manner or by radio link to a cardiovascular sensor 14, which is designed as a chest strap. The smartwatch 30 is preferably connected by way of a radio link, for example by way of a mobile radio link, to the computing unit 16, which is designed here by way of example as a cloud server. According to one embodiment, on the cloud server there are user data of a number of users, which to the cloud server by means of mobile and/or stationary computers or respectively by means of a device 10, in particular via the Internet.

Furthermore, FIG. 2 shows that the user 5 wears glasses 32, which are part of the device 10 and preferably act as an output unit 18.2. Preferably, the glasses 32 are augmented reality glasses. The glasses also comprise a sensor for a pupil reaction, which represents an additional brain activity sensor 18.2. Also provided as an input device 24 is a microphone, which in the embodiment shown is arranged on the glasses 32. In a further embodiment, the microphone is connected to the headphones or is designed as a single part.

Here by way of example the user is running on a cardio device 26, which is designed as a treadmill, which in particular is not connected to the device. In a further embodiment it is provided that the user trains without a cardio device, for example jogs, walks, hikes, rows or performs some other physical activity that leads to an increase in heart rate. In the example shown, the device comprises an electrostimulation device 28, which influences a training effect, in particular the heart rate of the user. The electrostimulation device 28 is arranged here by way of example on the thighs of the user 5. In a further embodiment it is provided that the electrostimulation device 28 is arranged at one or more desired locations of a body of the user 5.

For example, the user 5 is training in a fitness studio on a cardio device 26. The sensor signals determined by the brain activity sensors 18.1 and/or 18.2 and also the sensor signals determined by the cardiovascular sensor 14 are converted by the smartwatch 30 into neuronal data and pulse data. By way of the mobile radio link, the smartwatch sends the neuronal data and the pulse data to the computing unit 16, which is designed as a cloud server on the Internet. The task algorithm 20 stored in the computing unit 16 determines a task 22 from a number of tasks that are stored in the computing unit 16. In particular, the task is only determined when pulse data and neuronal data provide essentially optimum conditions for neuroplasticity, possibly while taking into consideration the user data. The task determined is sent to the smartwatch 30, in order to output it by means of the output unit 18.1 and/or 18.2. If optimum conditions for neuroplasticity by means of the task algorithm are still not yet evident, the computing unit 16 in one embodiment sends either tasks that influence a brain activity and/or signals for controlling the electrostimulation device 28. One embodiment also provides that the user 5 receives feedback concerning his neuronal data and/or his pulse data, which are for example graphically output by means of the output unit 18.2. The user can base his physical training for example on the pulse data. In particular, it is displayed to the user, preferably graphically or in color, whether he has an essentially optimum training pulse for neuroplasticity. It is also provided in one embodiment that auditory and/or visual stimuli are output to the user by way of the output unit 18.1 and/or 18.2, in particular for the stimulation of the brain activity.

After output of the task, the user answers it verbally, wherein the input device 24 receives a voice input and passes it on to the smartwatch 30 or to the computing unit 16 for evaluation. After that, a further determination of a further task 22 takes place, possibly after a time interval. In particular, at least one previous task 22 and in each case an answer to the at least one previous task 22 are taken into consideration in the determination of the new task 22.

The invention claimed is:

1. A device for neurovascular stimulation, comprising:
at least one brain activity sensor which generates both neuronal data and measurements of the flow of blood through a subject's brain,
at least one cardiovascular sensor,
at least one computing unit,
wherein the computing unit is configured or configurable for using at least one task algorithm,
at least one output unit, and
a cardio device and/or an electrostimulation device,
wherein signals from the at least one brain activity sensor and the at least one cardiovascular sensor are received by the at least one computing unit and the at least one computing unit uses the task algorithm and the signals from both the at least one brain activity sensor and the at least one cardiovascular sensor to control the cardio device and/or the electrostimulation device in such a way that a user achieves a pulse rate, a brain neural response, and a brain vascular response that is optimized for neurovascular plasticity.

2. The device as claimed in claim 1, further comprising at least one input device in communication with the at least one computing unit.

3. The device as claimed in claim 1 wherein the signals of the at least one brain activity sensor comprise neuronal data and wherein the signals of the at least one cardiovascular sensor comprises pulse data, and wherein the neuronal data and pulse data are settable in relation to one another by the at least one task algorithm.

4. A method for controlling neurovascular stimulation, comprising:
providing a subject with a device comprising at least one brain activity sensor which generates both neuronal data and measurements of the flow of blood through a subject's brain, at least one cardiovascular sensor, at least one computing unit configured or configurable for using at least one task algorithm, at least one output unit, and a cardio device and/or an electrostimulation device;
receiving signals from both the at least one brain activity sensor and the at least one cardiovascular sensor by the at least one computing unit,
outputting at least one task using the at least one task algorithm on the at least one computing unit based on the signals from both the at least one brain activity sensor and the at least one cardiovascular sensor; and
controlling the cardio device and/or the electrostimulation device according to the at lease on task in such a way that a user achieves a pulse rate, a brain neural response, and a brain vascular response that is optimized for neurovascular plasticity.

5. The method as claimed in claim 4, further comprising determining neuronal data from the signals of the at least one brain activity sensor.

6. The method as claimed in claim 4, further comprising determining pulse data from the signals of the at least one cardiovascular sensor.

7. The method as claimed in claim 4, further comprising
determining neuronal data from the signals of the at least one brain activity sensor,
determining pulse data from the signals of the at least one cardiovascular sensor, and
determining the at least one task on the basis of a relation of at least one pulse data element of the pulse data to a neuronal data element of the neuronal data by the at least one task algorithm.

8. The method as claimed in claim 4, further comprising inputting input data to the at least one computing unit using an input device, and wherein the outputting step is also performed on the basis of at least one correlation with the input data.

9. The method as claimed in claim 4 wherein the at least one output task provides for a performance resistance of the cardio device and/or electrostimulation device, and wherein the performance resistance is controlled at least on the basis of a relation of at least one pulse data element determined from the at least one brain activity sensor to a neuronal data element determined from the at least one cardiovascular sensor.

* * * * *